(12) United States Patent
Duindam et al.

(10) Patent No.: US 12,343,094 B2
(45) Date of Patent: Jul. 1, 2025

(54) SYSTEMS AND METHODS FOR USING TRACKING IN IMAGE-GUIDED MEDICAL PROCEDURE

(71) Applicant: INTUITIVE SURGICAL OPERATIONS, INC., Sunnyvale, CA (US)

(72) Inventors: Vincent Duindam, San Francisco, CA (US); Federico Barbagli, San Francisco, CA (US); Timothy D. Soper, San Jose, CA (US); Tao Zhao, Sunnyvale, CA (US); Caitlin Q. Donhowe, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/653,383

(22) Filed: May 2, 2024

(65) Prior Publication Data
US 2024/0277421 A1 Aug. 22, 2024

Related U.S. Application Data

(60) Division of application No. 17/666,096, filed on Feb. 7, 2022, now Pat. No. 12,011,232, which is a
(Continued)

(51) Int. Cl.
*A61B 34/20* (2016.01)
*A61B 1/005* (2006.01)
(Continued)

(52) U.S. Cl.
CPC ............. *A61B 34/20* (2016.02); *A61B 1/005* (2013.01); *A61B 1/009* (2022.02); *A61B 1/2676* (2013.01);
(Continued)

(58) Field of Classification Search
CPC ......... A61B 34/20; A61B 1/005; A61B 1/009; A61B 1/2676; A61B 5/064;
(Continued)

(56) References Cited

U.S. PATENT DOCUMENTS 6,288,783 B1 9/2001 Auad
6,380,732 B1 4/2002 Gilboa
(Continued)

FOREIGN PATENT DOCUMENTS

CN 101320005 A 12/2008
CN 101918073 A 12/2010
(Continued)

OTHER PUBLICATIONS

International Preliminary Report on Patentability for Application No. PCT/US2016/051139, mailed on Mar. 22, 2018, 10 pages (ISRG06890/PCT).
(Continued)

*Primary Examiner* — Adil Partap S Virk
(74) *Attorney, Agent, or Firm* — Haynes & Boone, LLP.

(57) ABSTRACT

A method comprises tracking a set of optical fiducials positioned on a reference portion of a medical instrument. The medical instrument includes an elongated flexible body with a distal end and a rigid proximal body which includes the reference portion. The method further comprises receiving shape information from a shape sensor extending within the medical instrument between the reference portion and the distal end and determining a pose of a portion of the elongated flexible body with respect to the patient anatomy.

20 Claims, 10 Drawing Sheets

Related U.S. Application Data continuation of application No. 15/759,129, filed as application No. PCT/US2016/051139 on Sep. 9, 2016, now Pat. No. 11,278,354.

(60) Provisional application No. 62/216,494, filed on Sep. 10, 2015.

(51) Int. Cl.

| | | |
|---|---|---|
| *A61B 1/267* | (2006.01) | |
| *A61B 5/06* | (2006.01) | |
| *A61B 17/00* | (2006.01) | |
| *A61B 34/00* | (2016.01) | |
| *A61B 34/10* | (2016.01) | |
| *A61B 90/00* | (2016.01) | |

(52) U.S. Cl.
CPC ........ *A61B 5/064* (2013.01); *A61B 17/00234* (2013.01); *A61B 90/39* (2016.02); *A61B 2017/003* (2013.01); *A61B 2017/00809* (2013.01); *A61B 2034/104* (2016.02); *A61B 2034/105* (2016.02); *A61B 2034/2051* (2016.02); *A61B 2034/2055* (2016.02); *A61B 2034/2061* (2016.02); *A61B 34/25* (2016.02); *A61B 2090/3614* (2016.02); *A61B 2090/363* (2016.02); *A61B 2090/364* (2016.02); *A61B 2090/365* (2016.02); *A61B 90/37* (2016.02); *A61B 2090/371* (2016.02); *A61B 2090/3983* (2016.02)

(58) Field of Classification Search
CPC ... A61B 17/00234; A61B 90/39; A61B 34/25; A61B 90/37; A61B 2017/003; A61B 2017/00809; A61B 2034/104; A61B 2034/105; A61B 2034/2051; A61B 2034/2055; A61B 2034/2061; A61B 2090/3614; A61B 2090/363; A61B 2090/364; A61B 2090/365; A61B 2090/371; A61B 2090/3983
See application file for complete search history.

(56) References Cited

U.S. PATENT DOCUMENTS

| | | | |
|---|---|---|---|
| 6,389,187 | B1 | 5/2002 | Greenaway et al. |
| 7,316,681 | B2 | 1/2008 | Madhani et al. |
| 7,772,541 | B2 | 8/2010 | Froggatt et al. |
| 8,900,131 | B2 | 12/2014 | Chopra et al. |
| 9,259,274 | B2 | 2/2016 | Prisco |
| 9,452,276 | B2 | 9/2016 | Duindam et al. |
| 11,278,354 | B2 * | 3/2022 | Duindam ............... A61B 90/39 |
| 12,011,232 | B2 * | 6/2024 | Duindam ............. A61B 1/2676 |
| 2003/0187351 | A1 | 10/2003 | Franck, I et al. |
| 2006/0013523 | A1 | 1/2006 | Childlers et al. |
| 2007/0185485 | A1 | 8/2007 | Hauck et al. |
| 2008/0139916 | A1 | 6/2008 | Maier et al. |
| 2008/0200794 | A1 | 8/2008 | Teichman et al. |
| 2009/0088775 | A1 | 4/2009 | Swarup et al. |
| 2009/0137952 | A1 | 5/2009 | Ramamurthy et al. |
| 2010/0030063 | A1 | 2/2010 | Lee et al. |
| 2011/0028894 | A1 | 2/2011 | Foley et al. |
| 2011/0166514 | A1 | 7/2011 | Trovato et al. |
| 2011/0237930 | A1 | 9/2011 | Donaldson et al. |
| 2011/0295268 | A1 | 12/2011 | Roelle et al. |
| 2012/0232547 | A1 | 9/2012 | Cohen |
| 2013/0150732 | A1 | 6/2013 | Manzke et al. |
| 2014/0052152 | A1 | 2/2014 | Au et al. |
| 2015/0031982 | A1 * | 1/2015 | Piferi ..................... A61B 6/032 600/417 |
| 2015/0351860 | A1 | 12/2015 | Piron et al. |
| 2016/0199148 | A1 * | 7/2016 | Maracaja-Neto .... A61B 1/0052 600/424 |
| 2017/0265953 | A1 | 9/2017 | Fenech et al. |
| 2018/0014888 | A1 | 1/2018 | Bonny et al. |
| 2018/0153621 | A1 | 6/2018 | Duindam et al. |
| 2018/0235709 | A1 | 8/2018 | Donhowe et al. |
| 2018/0240237 | A1 | 8/2018 | Donhowe et al. |
| 2018/0360551 | A1 | 12/2018 | Ogawa et al. |
| 2022/0160436 | A1 | 5/2022 | Duindam et al. |

FOREIGN PATENT DOCUMENTS

| | | |
|---|---|---|
| CN | 201968657 U | 9/2011 |
| WO | WO-2012158324 A2 | 11/2012 |
| WO | WO-2014150509 A1 | 9/2014 |
| WO | WO-2016018618 A1 | 2/2016 |
| WO | WO-2016164311 A1 | 10/2016 |
| WO | WO-2016191298 A1 | 12/2016 |
| WO | WO-2017030913 A2 | 2/2017 |
| WO | WO-2017030915 A1 | 2/2017 |

OTHER PUBLICATIONS

International Search Report and Written Opinion for Application No. PCT/US2016/051139, mailed on Jan. 19, 2017, 14 pages (ISRG06890/PCT).

Medtronic, Treon Treatment Guidance System System Manual, Part No. 9680169, revision 10, 2005, 46 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

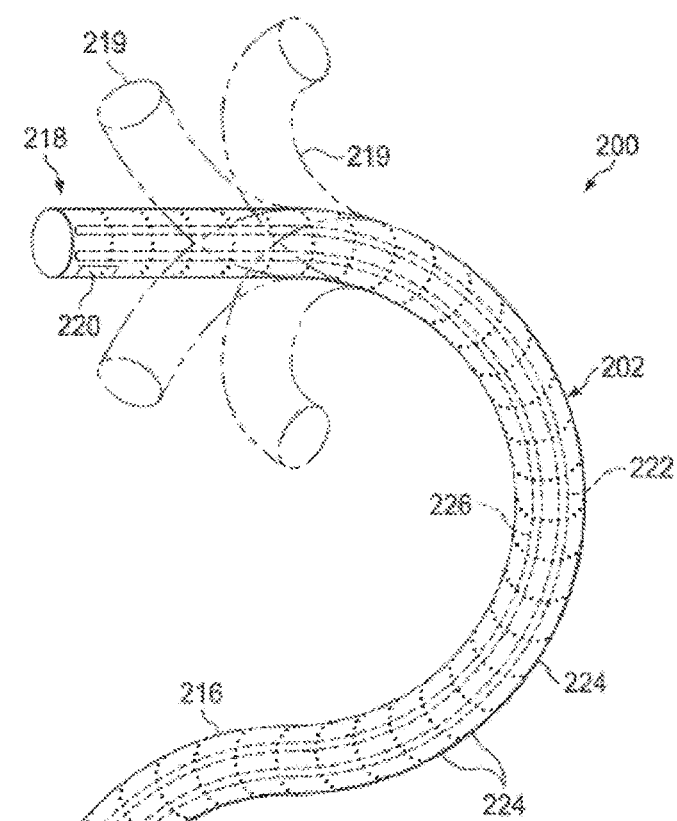
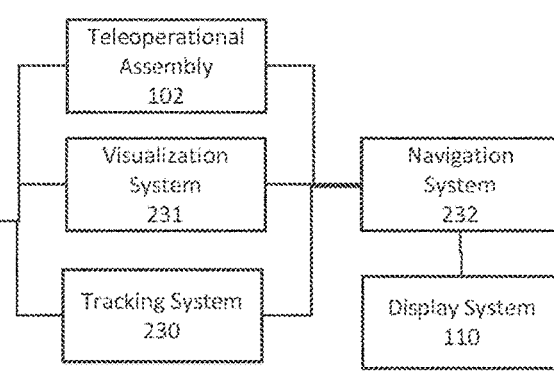
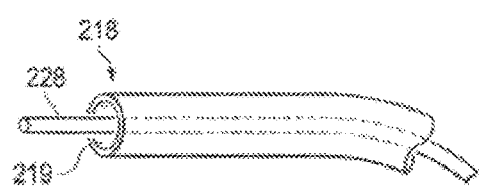
FIG. 2A
FIG. 2B

SYSTEMS AND METHODS FOR USING TRACKING IN IMAGE-GUIDED MEDICAL PROCEDURE

CROSS-REFERENCE TO RELATED APPLICATIONS

This Application is a divisional of U.S. application Ser. No. 17/666,096 filed Feb. 7, 2022, which is a continuation of U.S. patent application Ser. No. 15/759,129 filed Mar. 9, 2018, which is the U.S. national phase of International Application No. PCT/US2016/051139, filed Sep. 9, 2016, which designated the U.S. and claims priority to and the benefit of Provisional Application Ser. No. 62/216,494, filed Sep. 10, 2015, the contents of all of which are hereby incorporated by reference in their entirety.

FIELD

The present disclosure is directed to systems and methods for conducting an image-guided procedure, and more particularly to systems and methods for using tracking systems during an image-guided procedure.

BACKGROUND

Minimally invasive medical techniques are intended to reduce the amount of tissue that is damaged during medical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be correlated with pre-operative or intra-operative images of the patient anatomy. With the image-guided instruments correlated to the images, the instruments may navigate natural or surgically created passageways in anatomic systems such as the lungs, the colon, the intestines, the kidneys, the heart, the circulatory system, or the like. Traditional instrument tracking and referencing systems may require the use of electromagnetic sensors which are subject to interference by metal objects in the surgical environment. Other tracking systems may require continuous lines of sight between cameras and fiducial markers thought the procedure, hampering the use of equipment and personnel in a crowded surgical environment. Systems and methods for performing image-guided surgery with minimal clinical disturbances are needed.

SUMMARY

The embodiments of the invention are summarized by the claims that follow the description.

In one embodiment, a method comprises tracking a set of optical fiducials positioned on a patient anatomy and tracking a set of optical fiducials positioned on a reference portion of a medical instrument. The medical instrument includes an elongated flexible body with a distal end and a rigid proximal body which includes the reference portion. The method further comprises receiving shape information from a shape sensor extending within the medical instrument between the reference portion and the distal end and determining a pose of a portion of the elongated flexible body with respect to the patient anatomy.

In another embodiment, a method comprises tracking a set of optical fiducials positioned on a reference portion of a medical instrument in a surgical environment. The medical instrument includes an elongated flexible body with a distal end and a rigid proximal body which includes the reference portion. The method also includes tracking a set of optical fiducials positioned on an insertion track of a teleoperational manipulator in the surgical environment. The rigid proximal body of the medical instrument is coupled to move along the insertion track. The method also includes calibrating a plurality of insertion measurements with respective positions of the reference portion of the rigid proximal body on the insertion track and determining a pose of a patient anatomy in the surgical environment. The method also includes driving movement of the rigid proximal body of the medical instrument to a first location along the insertion track and determining a pose of the elongated flexible body with respect to the patient anatomy in the surgical environment when the rigid proximal body is in the first location along the insertion track.

In another embodiment, a method comprises tracking, as a first medical procedure is performed, a set of optical fiducials in a teleoperational system and determining movement of the set of optical fiducials in the teleoperational system. The method also includes operating the teleoperational system to conduct a second medical procedure based on the movement.

In another embodiment, a teleoperational medical system comprises an instrument carriage, a medical instrument coupled to the instrument carriage, a shape sensor, a first set of optical fiducials, a tracking sensor, and a control system. The medical instrument comprises an elongated flexible body with a distal end and a rigid proximal body, the rigid proximal body comprising a reference portion. The shape sensor extends along the medical instrument between the reference portion and the distal end. The first set of optical fiducials is configured to be positioned on the reference portion. The tracking sensor is configured to track the first set of optical fiducials. The control system is configured to operate the optical tracking sensor to track a first configuration of the first set of optical fiducials, receive shape information from the shape sensor, and determine a pose of a portion of the elongated flexible body with respect to a patient anatomy.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a teleoperational medical system, in accordance with embodiments of the present disclosure.

FIG. 2A illustrates a medical instrument system utilizing aspects of the present disclosure.

FIG. 2B illustrates a distal end of the medical instrument system of FIG. 2A with an extended medical tool, in accordance with embodiments of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
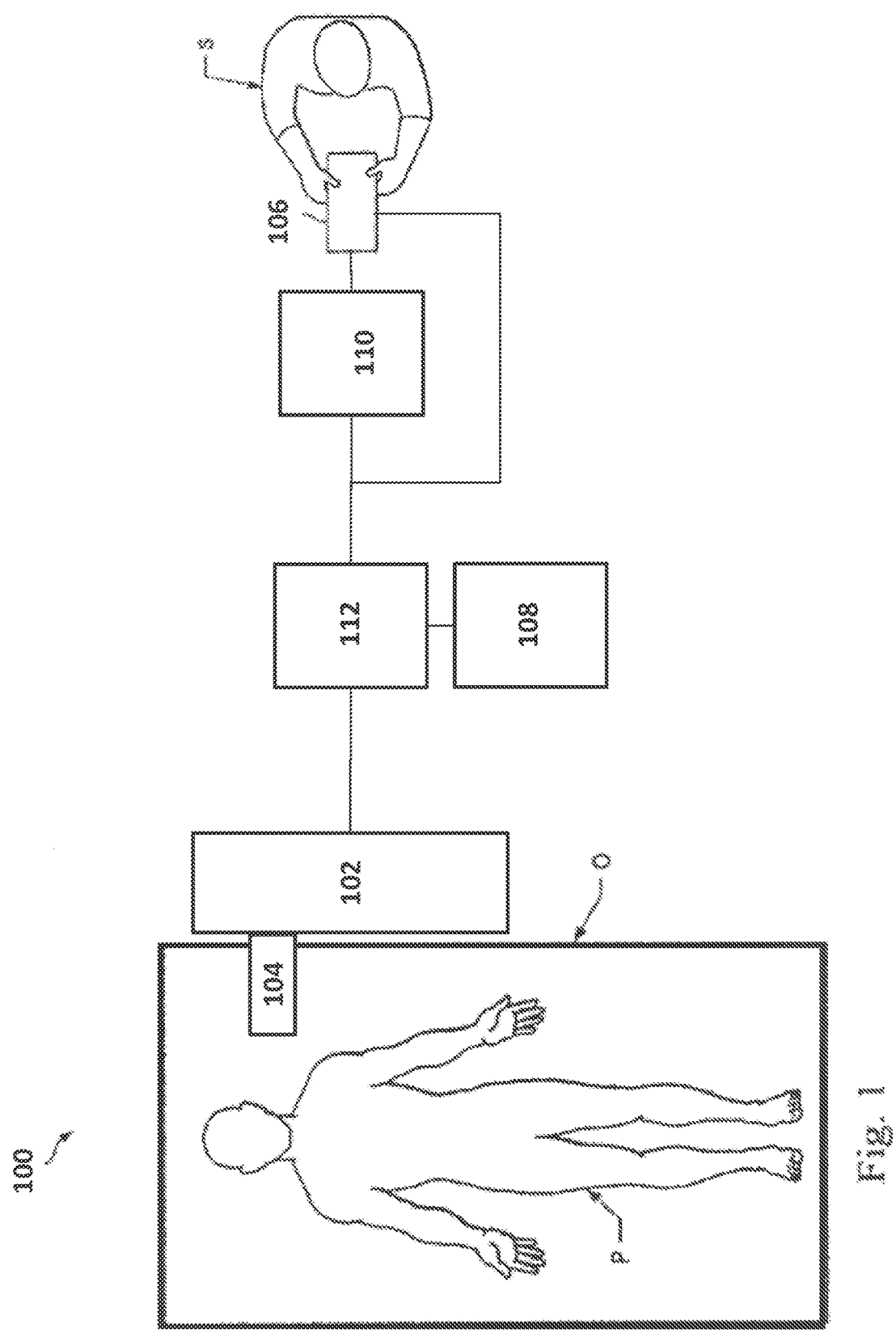

Referring to FIG. 1 of the drawings, a teleoperational medical system for use in, for example, surgical, diagnostic, therapeutic, or biopsy procedures, is generally indicated by the reference numeral 100. As shown in FIG. 1, the teleoperational system 100 generally includes a teleoperational manipulator assembly 102 for operating a medical instrument 104 in performing various procedures on the patient P. The manipulator assembly 102 is mounted to or near an operating table O. An operator input system 106 allows the operator (e.g. a clinician or surgeon or some other personnel) S to view the interventional site and to control the manipulator assembly 102 as a slave manipulator assembly. In such cases, the operator input system can also be termed the master assembly. A single manipulator assembly 102, medical instrument 104, and operator input system 106 is shown in FIG. 1. However, it should be understood that various teleoperated systems may have a plurality of manipulator assemblies, medical instruments, master assemblies, or combination thereof.

The operator input system 106 may be located at a surgeon's console which is usually located in the same room as operating table O. However, it should be understood that the operator S can be located in a different room or a completely different building or be geographically remote from the patient P. Operator input system 106 generally includes one or more control devices for controlling the manipulator assemblies 102. The control devices may include any number of a variety of input devices or sensors, such as joysticks, trackballs, data gloves, trigger-guns, hand-operated controllers, eye tracking devices, voice recognition devices, body motion or presence sensors, or the like. In some embodiments, the control devices will be provided with the same degrees of freedom as one or more associated medical instruments systems (such as medical instrument 104) to provide the operator with telepresence, or the perception that the control devices are integral with the medical instrument systems so that the operator has a sufficiently strong sense of directly controlling the medical instrument systems. In other embodiments, the control devices may have more or fewer or different degrees of freedom than the one or more associated medical instrument systems (such as medical instrument 104) and still provide the operator with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational manipulator assembly 102 supports the medical instrument 104 and may include a kinematic structure of one or more non-servo controlled links (e.g., one or more links that may be manually positioned and locked in place, generally referred to as a set-up structure) and a teleoperational manipulator. The teleoperational manipulator assembly 102 includes a plurality of actuators or motors that drive inputs on the medical instrument 104 in response to commands from the control system (e.g., a control system 112). The motors include drive systems that when coupled to the medical instrument 104 may advance the medical instrument 104 into a naturally or surgically created anatomic orifice. Other motorized drive systems may move the distal end of the medical instrument 104 in multiple degrees of freedom, which may include three degrees of translational motion (e.g., translational motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position or speed sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the sub-assemblies of the teleoperational medical system 100 including instruments of the teleoperational assembly 102. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of medical instrument 104; a visualization system for capturing images from the distal end of the catheter system; other sensor systems based on various sensor technologies; or a combination thereof.

The visualization system (e.g., visualization system 231 of FIG. 2A) may include a viewing scope assembly that records a concurrent or real-time image of the surgical site and provides the image to the operator (e.g. clinician or surgeon or other personnel) S. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument 104 and the operator input system 106 with the perception of telepresence.

The display system 110 may also display an image of the surgical site and medical instruments (e.g. medical instrument 104) captured by the visualization system. The display 110 and the control devices may be oriented such that the relative positions of the imaging device in the scope assembly and the medical instruments are similar to the relative positions of the operator's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display 110 may display a virtual navigational image in which the actual location of the medical instrument 104 is registered (i.e., dynamically referenced) with the pre-operative or concurrent images/model to present the operator (e.g. clinician or surgeon or other personnel) S with a virtual image of the internal surgical site from the viewpoint of the location of the tip of the instrument 104. An image of the tip of the instrument 104 or other graphical or alphanumeric indicators may be superimposed on the virtual image to assist the operator controlling the medical instrument. Alternatively, the instrument 104 may not be visible in the virtual image.

In other embodiments, the display 110 may display a virtual navigational image in which the actual location of the medical instrument is registered with preoperative or concurrent images to present the clinician or operator S with a virtual image of medical instrument within the surgical site from an external viewpoint. An image of a portion of the medical instrument or other graphical or alphanumeric indicators may be superimposed on the virtual image to assist the operator controlling the instrument 104.

The teleoperational medical system 100 also includes a control system 112. The control system 112 includes at least one memory and at least one computer processor (not shown), and in some embodiments typically a plurality of processors, for effecting control between the medical instrument 104, the operator input system 106, the sensor system 108, and the display system 110. The control system 112 also includes programmed instructions (e.g., a computer-readable medium storing the instructions) stored on non-transitory processor readable storage medium to implement some or all of the methods described in accordance with aspects disclosed herein, including instructions for providing pathological information to the display system 110. While control system 112 is shown as a single block in the simplified schematic of FIG. 1, the control system 112 may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports one or more wired or wireless communication protocols. Wireless communications protocols include examples such as Bluetooth, IrDA, HomeRF, IEEE 802.11, DECT, and Wireless Telemetry.

In some embodiments, control system 112 may include one or more servo controllers that receive force and/or torque feedback from one or more medical instrument systems (such as medical instrument 104). Responsive to the feedback, the servo controllers transmit signals to the operator input system 106. The servo controller(s) may also transmit signals instructing teleoperational assembly 102 to move the medical instrument system(s) (such as medical instrument 104) which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly 102 are provided as part of a teleoperational arm cart configured to be positioned adjacent to the patient's body during a surgical procedure.

The control system 112 may further include a virtual visualization system to provide navigation assistance to the one or more medical instrument systems (e.g. medical instrument 104) when used in an image-guided surgical procedure. Virtual navigation using the virtual visualization system is based upon reference to the acquired preoperative or intraoperative dataset of the anatomic passageways. More specifically, the virtual visualization system processes images of the surgical site imaged using imaging technology, including imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, a combination thereof, or the like. Software alone or in combination with manual input is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using electromagnetic (EM) sensor, fiber optic sensors, or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, suction systems, other systems, or combinations thereof. In alternative embodiments, the teleoperational system 100 may include more than one teleoperational assembly 102 and/or more than one operator input system 106. The exact number of teleoperational manipulator assemblies will depend on the surgical procedure and the space constraints within the operating room, among other factors. The operator input systems may be collocated or they may be positioned in separate locations that are geographically close or remote from each other. Multiple operator input systems allow more than one operator to control one or more manipulator assemblies in various combinations.

FIG. 2A illustrates a medical instrument system 200 in accordance aspects of the present disclosure, which may be used as the medical instrument 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, shape, or other physical characteristic of the catheter tip at distal end 218 and/or of one or more segments 224 along the body 216. The entire length of the body 216, between the distal end 218 and the proximal end 217, may be effectively divided into the segments 224. If the instrument system 200 is a medical instrument 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor 222 and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller. The optical fiber of the shape sensor 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the temporal history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as a plurality of electromagnetic (EM) sensors positioned along multiple locations of the catheter, can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system 200 may, optionally, include a position sensor system 220. The position sensor system 220 may be a component of an EM sensor system with the sensor 220 including one or more conductive coils that may be subjected to an externally generated electromagnetic field. In such an implementation, each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, clip appliers, etc. Examples of electrically activated end effectors include electrosurgical electrodes, transducers, sensors, and the like. In various embodiments, the medical tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly such as teleoperational assembly 102, the housing 204 may include drive inputs that removably couple to and receive power from motorized drive elements of the teleoperational assembly. In embodiments in which the instrument system 200 is manually operated in whole or in part, the housing 204 may include gripping features, manual actuators, or other components for manually controlling the motion of the instrument system 200. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The medical instrument system 200 is also suited for navigation and treatment of other tissues, via natural or surgically created connected passageways, in any of a variety of anatomic systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument system 200. The control system 116 may utilize the position information as feedback for positioning the instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In the embodiment of FIG. 2A, the instrument system 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

As shown in greater detail in FIG. 2B, medical tools (such as medical tool 228) for such procedures as surgery, biopsy, ablation, illumination, irrigation, or suction can be deployed through the channel 221 of the flexible body 216 and used at a target location within the anatomy. If, for example, the medical tool 228 is a biopsy instrument, it may be used to remove sample tissue or a sampling of cells from a target anatomic location. The medical tool 228 may be used with an image capture probe also within the flexible body 216. Alternatively, the medical tool 228 may itself be the image capture probe. The medical tool 228 may be advanced from the opening of the channel 221 to perform the procedure and then retracted back into the channel when the procedure is complete. The medical tool 228 may be removed from the proximal end 217 of the catheter flexible body or from another optional instrument port (not shown) along the flexible body.

Figure 3:
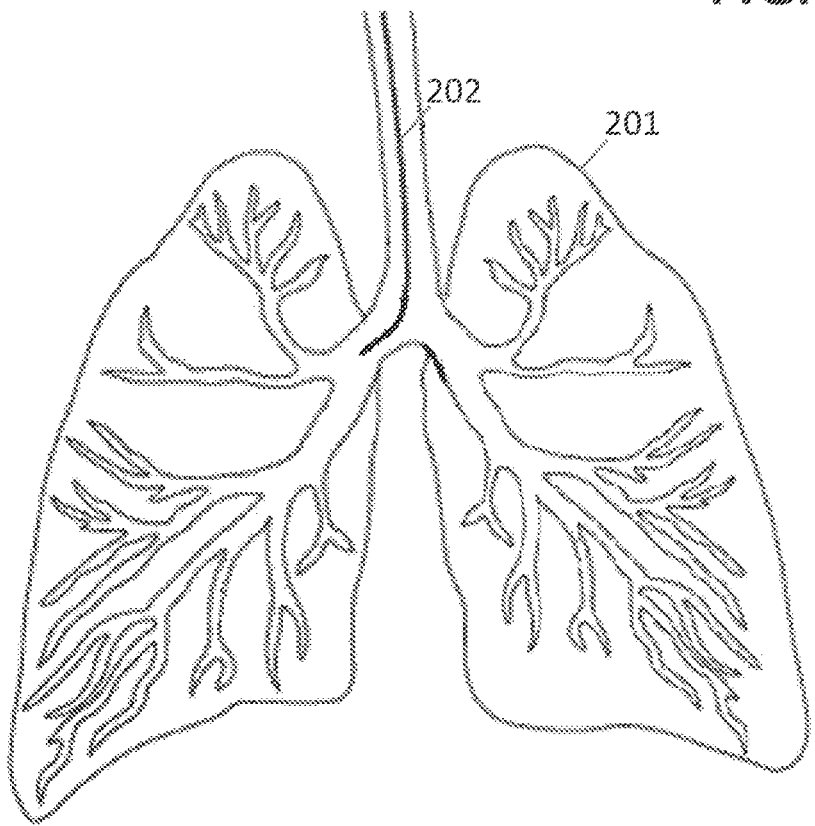
FIG. 3 illustrates the distal end of the medical instrument system of FIG. 2A positioned within a human lung.

FIG. 3 illustrates the catheter system 202 positioned within an anatomic passageway of a patient anatomy. In this embodiment, the anatomic passageway is an airway of human lungs 201. In alternative embodiments, the catheter system 202 may be used in other passageways of an anatomy.

Figure 4:
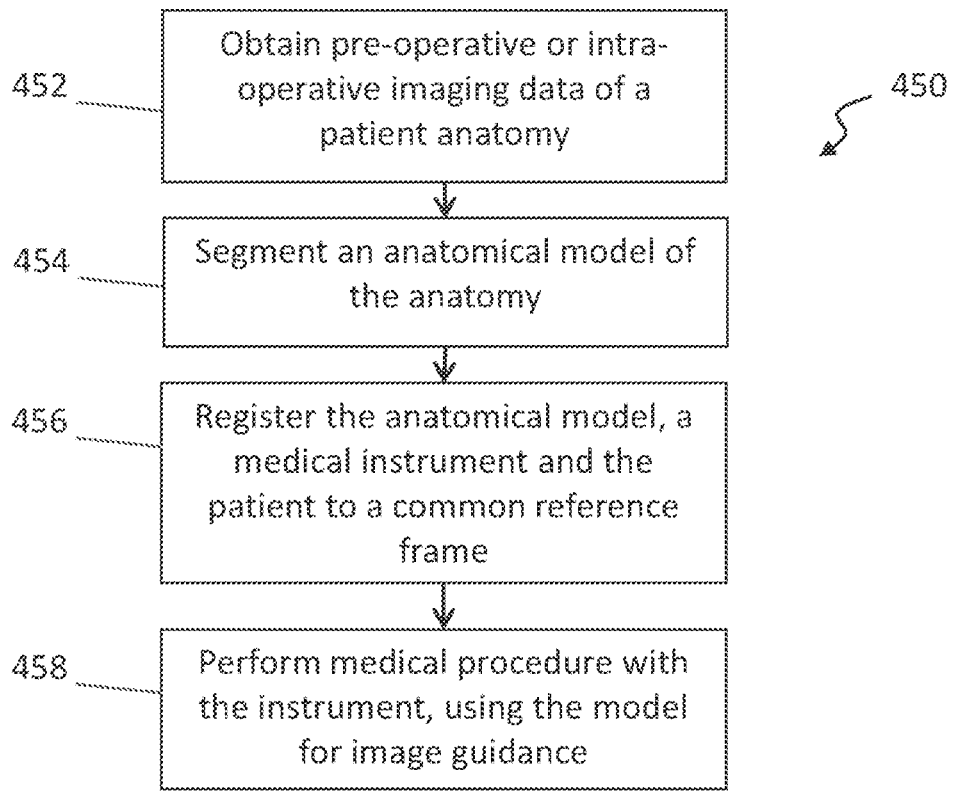
FIG. 4 is a flowchart illustrating a method used to provide guidance in an image-guided surgical procedure according to an embodiment of the present disclosure.

FIG. 4 is a flowchart illustrating a general method 450 for use in an image-guided surgical procedure in accordance with embodiments of the present disclosure. At a process 452, pre-operative or intra-operative image data is obtained using imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, or another imaging technique. The pre-operative or intra-operative image data may correspond to two-dimensional, three-dimensional, or four-dimensional (including e.g., time based or velocity based information) images. For example, the image data may represent the human lungs 201 of FIG. 3.

At a process 454, computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as a marching cube function or another appropriate function, to generate a 3D surface that encloses the voxels. The model may be made by any appropriate technique. For example, the model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 456, the anatomic model data, a medical instrument used to perform the medical procedure (e.g., instrument system 200), and the patient anatomy are co-registered in a common reference frame prior to and/or during the course of an image-guided surgical procedure on the patient. The common reference frame may be, for example, the surgical environment reference frame or the patient reference frame. The process 456 includes localizing the medical instrument with respect to the patient. The process 456 also includes registering the anatomic model with respect to the patient. At a process 458, the medical procedure may be performed using the anatomic model data to guide movement of the medical instrument.

Traditional registration methods for use with image-guided surgery often involve the use of technologies based on electromagnetic or impedance sensing. Metallic objects or certain electronic devices used in the surgical environment may create disturbances that impair the quality of the sensed data. Alternatively, registration may be performed using optical tracking systems. Optical tracking systems may be used to calculate the location and orientation of a medical instrument and patient within the coordinate system of the surgical environment. An optical tracking system uses a position sensor to detect infrared-emitting or retro-reflective markers attached to the teleoperational assembly, the medical instrument, and/or patient. The position sensor calculates the position and orientation of the teleoperational assembly, the medical instrument, and/or patient based on the information the position sensor receives from those markers. More specifically, optical tracking systems use data captured from image sensors to triangulate the three dimensional pose of the teleoperational assembly, the medical instrument, and/or patient between cameras calibrated to provide overlapping projections.

Optical tracking system have traditionally been used with physically non-flexible surgical instruments because the instrument's rigidity allows for reliable calculation of the position of the distal tip of the instrument based on the tracked position and orientation of the proximal end of the instrument, which is generally outside of the patient anatomy and thus visible to the optical tracking system. Optical tracking systems also typically require a clear line of sight between the tracking cameras and sensors and the fiducial markers. These requirements may limit the use of optical tracking in a clinical setting, especially one crowded with personnel and equipment or where the surgeon is remote from the patient. In various embodiments, the systems described within this disclosure allow for the use of optical tracking systems with flexible instruments. Additionally, in various methods described within this disclosure, the use of optical tracking may be reduced or minimized when the patient is stationary, thus reducing or eliminating the line-of-sight requirements during large portions of the medical procedure.

Figure 5:
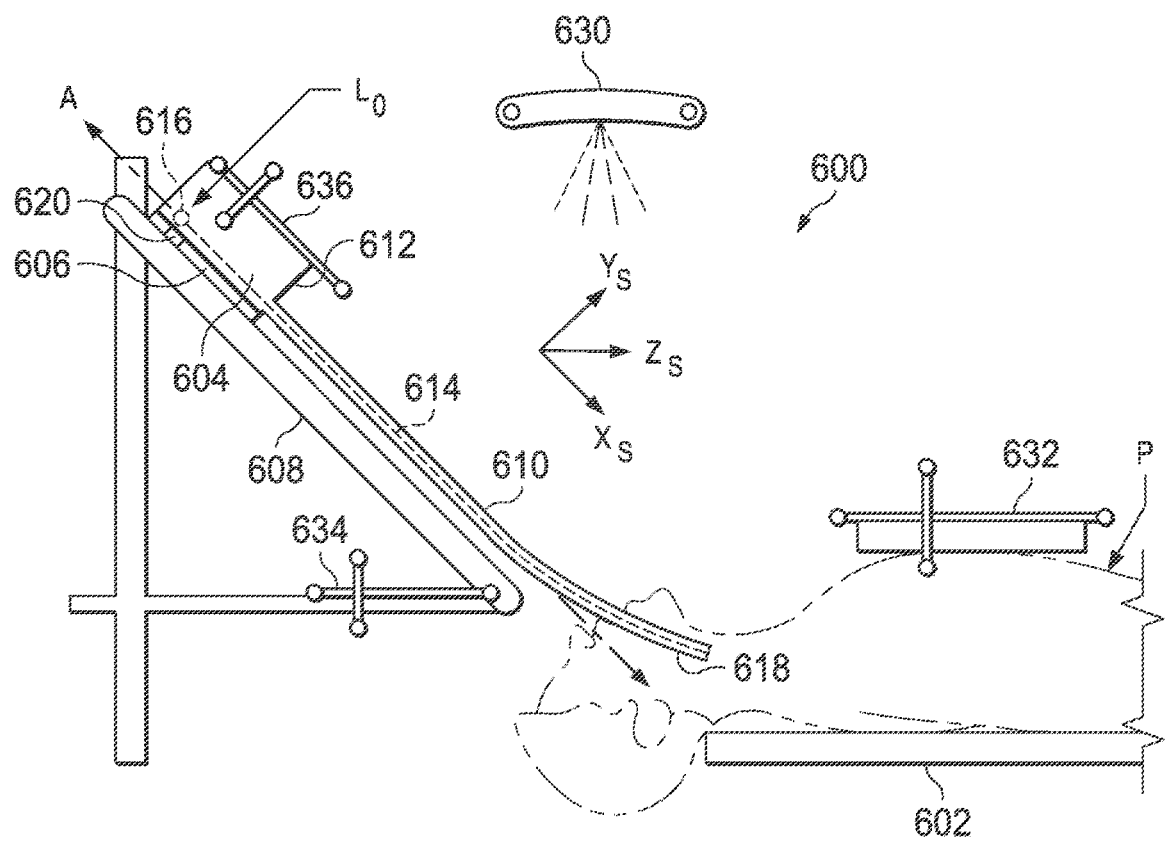
FIG. 5 is a side view of a patient coordinate space including a medical instrument mounted on an insertion track and an optical tracking system according to an embodiment of the present disclosure.

FIG. 5 illustrates an exemplary surgical environment 600 according to some embodiments, with a surgical coordinate system XS, YS, ZS, in which a patient P is positioned on a platform 602. The patient P may be stationary within the surgical environment in the sense that gross patient movement is limited by sedation, restraint, or other means. Cyclic anatomic motion including respiration and cardiac motion of the patient P may continue, unless the patient temporarily suspends respiratory motion. Within the surgical environment 600, a medical instrument 604 is coupled to an instrument carriage 606. The instrument carriage 606 is mounted to an insertion stage 608; in various embodiments, the insertion stage 608 may be fixed or movable within the surgical environment 600. The instrument carriage 606 may be a component of a teleoperational manipulator assembly (e.g., assembly 102) that couples to the instrument 604 to control insertion motion of the instrument 604 (i.e. motion in an XS direction using the coordinate system and configuration shown in FIG. 5) and, optionally in addition or in place of insertion motion, motion of a distal end of the instrument in one or multiple directions including rotational degrees of freedom such as yaw, pitch, and roll. The instrument carriage 606 or the insertion stage 608 may include servomotors (not shown) that control motion of the instrument carriage 606 along the insertion stage 608. The insertion stage 608 can be any appropriate insertion system that guides some or all of the motion of instrument carriage 606, and may be referred to as insertion track 608.

The medical instrument 604 may include a flexible catheter 610 coupled to a proximal rigid instrument body 612. In the embodiment shown in FIG. 5, the rigid instrument body 612 is coupled and fixed relative to the instrument carriage 606. In the illustrated embodiment, an optical fiber shape sensor 614 is fixed proximally on the rigid instrument body 612 at a reference point 616 of the optical fiber shape sensor 614. In an alternative embodiment, the point 616 of the sensor 614 is movable along the rigid instrument body 612, but the location of the reference point 616 may be determined from the physical configuration of the system (e.g., via data a tracking sensor or other tracking device, via data from a detection sensor, etc.). In these embodiments, the location of the reference point 616 of the optical fiber shape sensor 614 relative to the rigid instrument body 612 can be determined. In the embodiment shown in FIG. 5, the shape sensor 614 measures a shape from the reference point 616 to another point such as the distal end 618 of the catheter 610. The medical instrument 604 may be substantially similar to the medical instrument system 200. The reference point 616 is referred to as a point for convenience of explanation; in various embodiments the reference may be a reference portion of the sensor 614.

Figure 9:
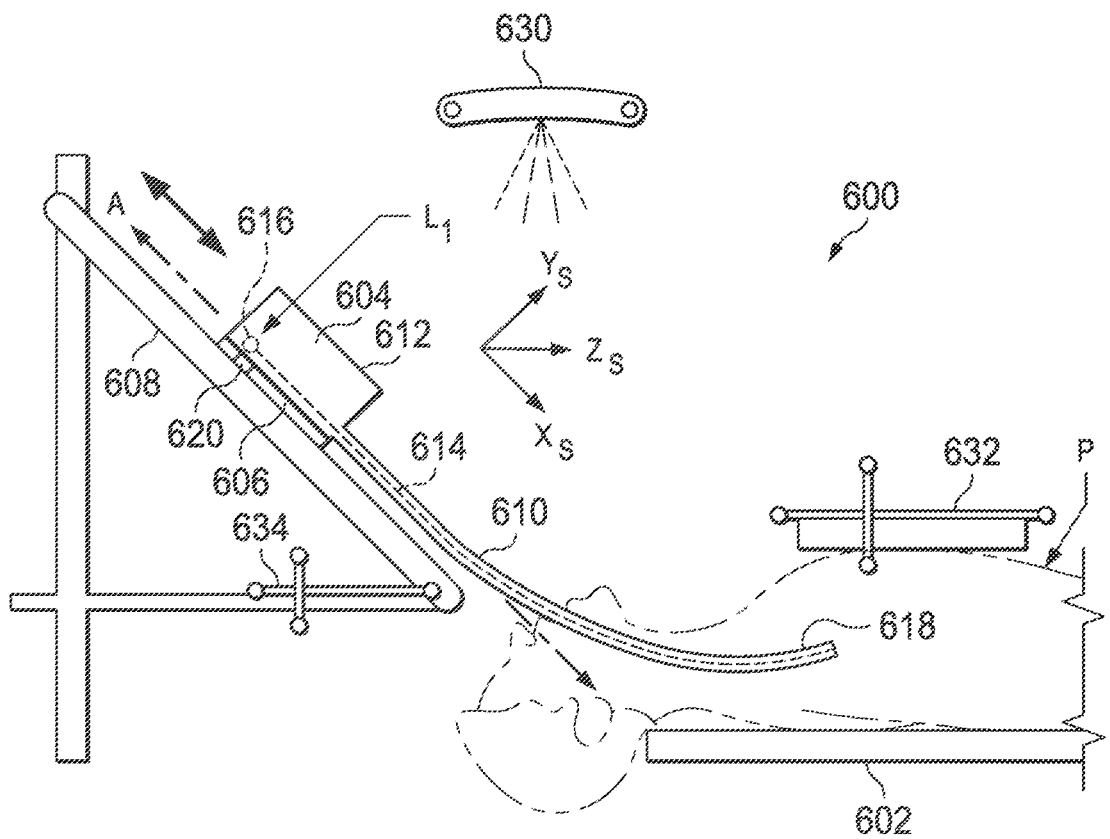
FIG. 9 is a side view of a patient coordinate space including a medical instrument mounted on an insertion track and an optical tracking system used in a medical procedure when the patient is non-stationary according to an embodiment of the present disclosure.
Figure 10:
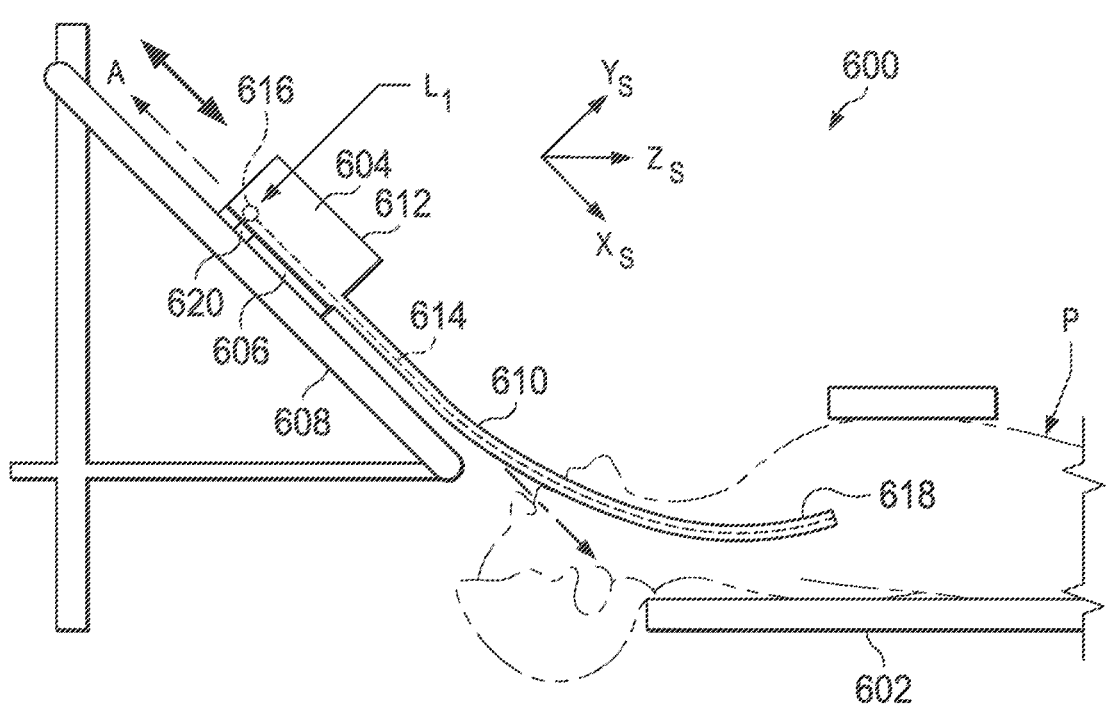
FIG. 10 is a side view of a patient coordinate space including a medical instrument mounted on an insertion track and an optical tracking system used in a medical procedure when the patient is stationary according to an embodiment of the present disclosure.

A position measuring device 620 provides information about the position of the rigid instrument body 612 as it moves on the insertion stage 608 along an insertion axis A. The position measuring device 620 may include any combination of resolvers, encoders, potentiometers, and mechanisms that determine the rotation and orientation of the motor shafts controlling the motion of the instrument carriage 606 and consequently the motion of the rigidly attached instrument body 612. In this embodiment, the insertion stage 608 is linear, but in alternative embodiments it may be curved or have a combination of curved and linear sections, such that the associated insertion path includes curved and linear sections. Optionally, the linear track may be collapsible as described, for example, in U.S. Provisional Patent Application No. 62/029,917 (filed Jul. 28, 2014) (disclosing "Guide Apparatus For Delivery Of A Flexible Instrument And Methods Of Use") which is incorporated by reference herein in its entirety. FIG. 5 shows the instrument body 612 and carriage 606 in a retracted position along the insertion stage 608. In this retracted position, the reference point 616 is at a position L0 on the axis A. In this position along the insertion stage 608 an XS component of the location of the point 616 may be set to a zero or original value in some embodiments. With this retracted position of the instrument body 612 and carriage 606, the distal end 618 of the catheter may be positioned just inside an entry orifice of the patient P. Also in this position, the position measuring device may be set to a zero or original value (e.g. I=0) in some embodiments. In FIGS. 9 and 10, the instrument body 612 and the carriage 606 have advanced along the linear track of the insertion stage 608 and the distal end of the catheter 610 has advanced into the patient P. In this advanced position shown in FIGS. 9 and 10, the reference point 616 is at a position L1 on the axis A.

FIG. 5 also illustrates an optical tracking system including an optical tracking sensor 630, a set of optical fiducial markers (fiducials) 632 positioned on the patient P, a set of optical fiducial markers (fiducials) 634 positioned on the insertion stage 608, and a set of optical fiducial markers (fiducials) 636 positioned on the rigid instrument body 612. The sets of fiducials 632, 634, 636 may be positioned on the patient P, the insertion stage 608 and the rigid instrument body 612, respectively, by being attached directly or indirectly to them. For example, the set of fiducials 632 may be adhered to patient, and the sets of fiducials 634, 636 may be adhered to or embedded in the insertion stage 608 or the rigid instrument body 612. As another example, the sets of fiducials 632, 634, 636 may be positioned on the patient P, the insertion stage 608, and the rigid instrument body 612, respectively, through one or more intermediate components.

In various embodiments, the sets of fiducial markers 632, 634, 636 comprise reflectors positioned on reference arrays, and the tracking sensor 630 comprises a pair of cameras capable of emitting and receiving infrared rays reflected by the reflectors of the sets of fiducial markers 632, 634, 636. In one embodiment, the fiducial markers are passive markers which include spherical, retro-reflective markers that reflect the infrared light emitted by illuminators on the tracking sensor 630. In alternative systems, the fiducial markers may be active infrared-emitting markers that are activated by an electrical signal. In further embodiments, the tracking system utilizes other visible or non-visible portions of the electromagnetic spectrum in addition or in place of infrared light. FIG. 5 shows each set of fiducial markers as comprising four fiducial markers arranged at the ends of a cross; other embodiments may use a different number and arrangement of fiducial markers. Further descriptions of optical tracking systems are provided, for example, in U.S. Pat. No. 6,288,783, filed Oct. 28, 1999, disclosing, "System for determining spatial position and/or orientation of one or more objects," which is incorporated by reference herein in its entirety.

Figure 6:
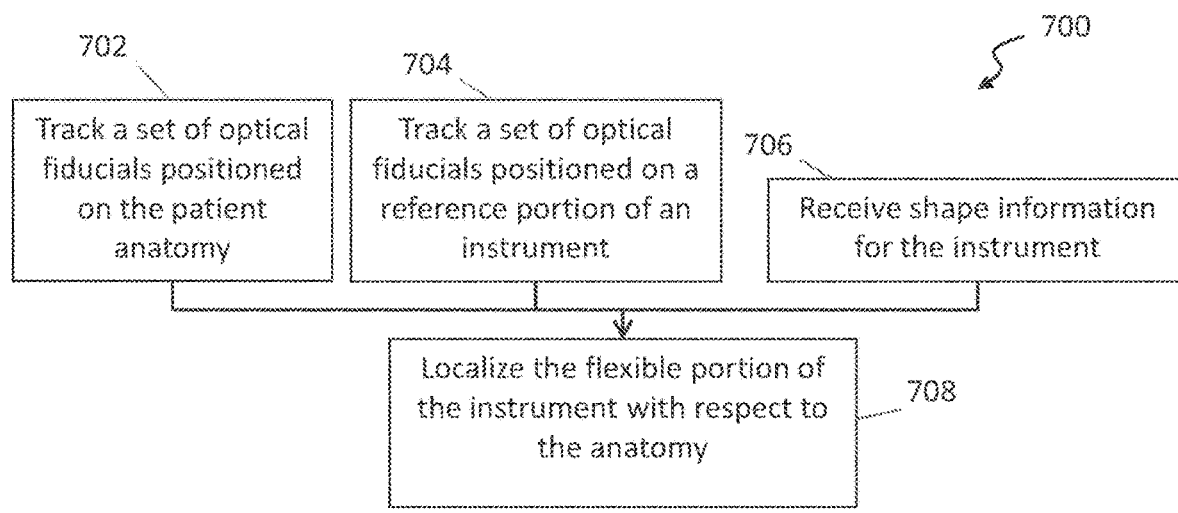
FIG. 6 illustrates a flowchart of a portion of an image-guided surgical procedure according to an embodiment of the present disclosure.

As described above for FIG. 4, a process 456 includes localizing the medical instrument (such as instrument system 200) with respect to the patient. FIG. 6 is a flowchart illustrates a method 700 in accordance with an embodiment of the present disclosure, used to localize the medical instrument with respect to the patient in the surgical environment. The methods of this description, including process 456 illustrated in FIG. 4 and method 700 illustrated in FIG. 6 as a set of blocks, steps, operations, or processes. Not all of the illustrated, enumerated operations may be performed in all embodiments of the process 456 or method 700. Also, the method 700 references the system of FIG. 5, however, fewer or more than all of the fiducial markers shown in FIG. 5 may be used to perform the method 700 in various embodiments. Additionally, some additional operations that are not expressly illustrated in the methods in this disclosure may be included before, after, in between, or as part of the enumerated processes. Some embodiments of the methods of this description include instructions that corresponded to the processes of the methods as stored in a memory. These instructions may be executed by a processor like a processor of the control system 112.

Thus, some embodiments of the method 700 may begin at a process 702, in which the set of optical fiducial markers 632 on the patient P is tracked by the optical tracking sensor 630 in the surgical environment 600. That is, the optical tracking sensor 630 monitors the configuration of the set of fiducial markers 632 by monitoring physical characteristics such as the absolute and relative location(s) and orientation (s) of fiducial markers in the set of fiducial marker 632. At a process 704, the optical tracking sensor 630 tracks the set of optical fiducial markers 636 attached to the rigid instrument body 612 as the instrument body 612 moves the flexible catheter 610 into or out of the patient anatomy. At a process 706, shape information from the shape sensor 614 is received. The shape information describes the shape of the sensor 614 extending between the reference point 616 on the rigid instrument body 612 and the distal end of the flexible catheter 610. The processes 702, 704, 706 may be performed concurrently or in a sequential order. Also, the processes 702, 704, or 706 may be performed a different number of times during a same time period. At a process 708, the flexible catheter 610 is localized with respect to the patient anatomy in the surgical environment. More specifically, the shape information combined with the location of the reference point 616 in the surgical environment, as tracked in process 704, is used to determine the position and orientation of the distal tip of the flexible catheter 610 and other points along the catheter 610 in the surgical environment. With the patient P also tracked by the optical tracking sensor 630 as described at process 702, the position and orientation of the patient P in the surgical environment can also be determined. Thus, the position and orientation of the flexible catheter 610 can be determined with respect to the patient anatomy in the surgical environment frame of reference. The processes 702-708 may be repeated throughout a medical procedure as the associated medical instrument is inserted or otherwise moved within the patient anatomy to provide current localization about the medical instrument relative to the anatomy and anatomical model.

In the method 700, the optical tracking system may be used throughout the medical procedure to track the movement of the medical instrument. However, using the optical tracking system throughout the procedure may be disruptive in a crowded surgical environment because the lines of sight between the fiducial markers and the sensor must remain clear for the optical tracking system to accurately operate.

Figure 7:
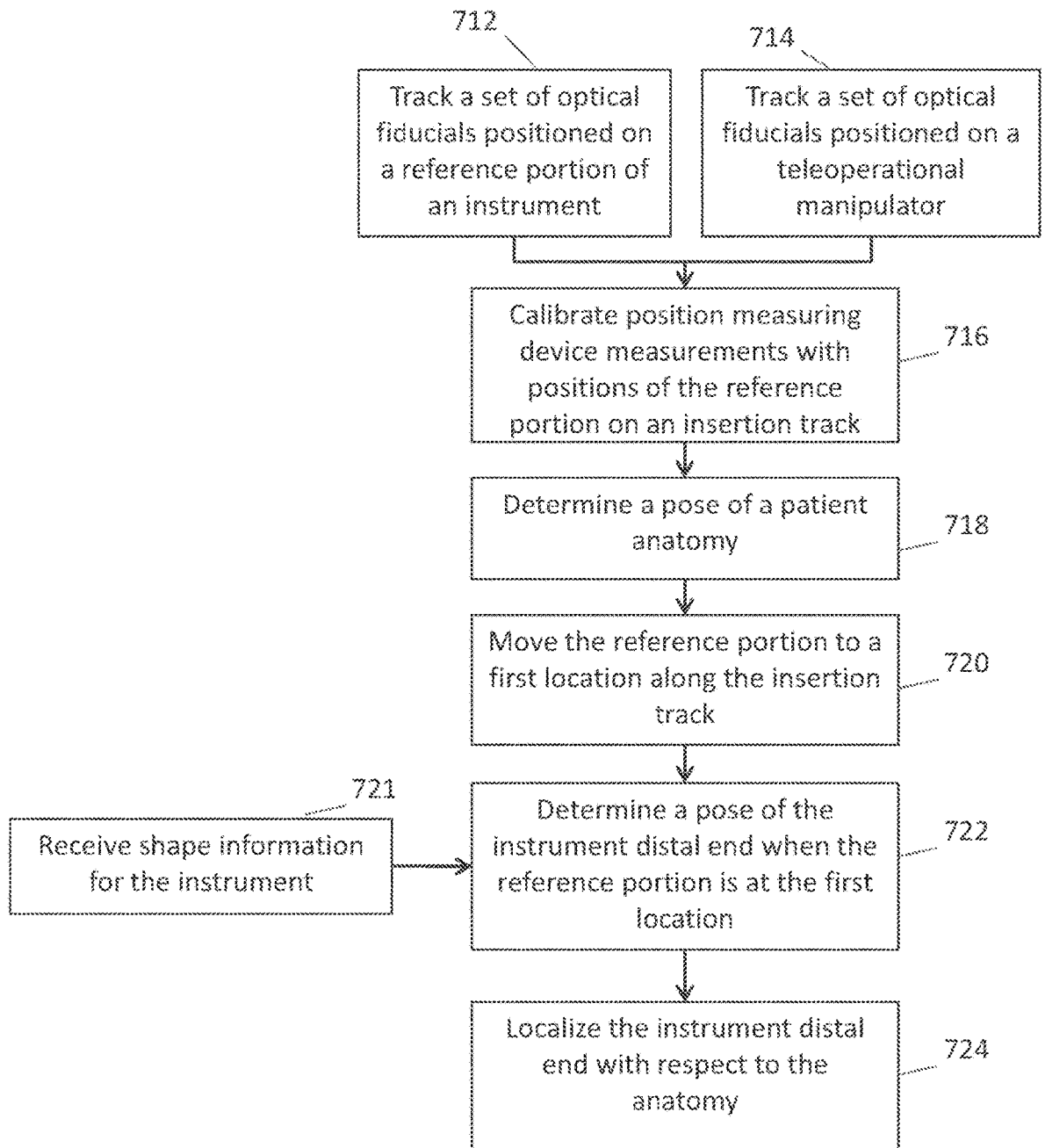
FIG. 7 illustrates a flowchart of a portion of an image-guided surgical procedure according to another embodiment of the present disclosure.

FIG. 7 illustrates a method 710 in accordance with an embodiment of the present disclosure which uses the optical tracking system during a calibration phase of the medical procedure. In various embodiments, the method 710 does not require continuous use of the optical tracking system throughout the medical procedure, and can be intermittent or continuous in various embodiments. For example, if the patient remains stationary within the surgical environment, or localization information is not needed continuously, the system may operate intermittently on a regular time schedule or on a manually controlled basis. In alternative embodiments, the calibration may be performed during a manufacturing or set-up process not contemporaneous with the medical procedure, and the calibration information stored in a memory of the system or instrument and retrieved from memory as appropriate. As the procedure is performed, the stored calibration information may be used.

Figure 8:
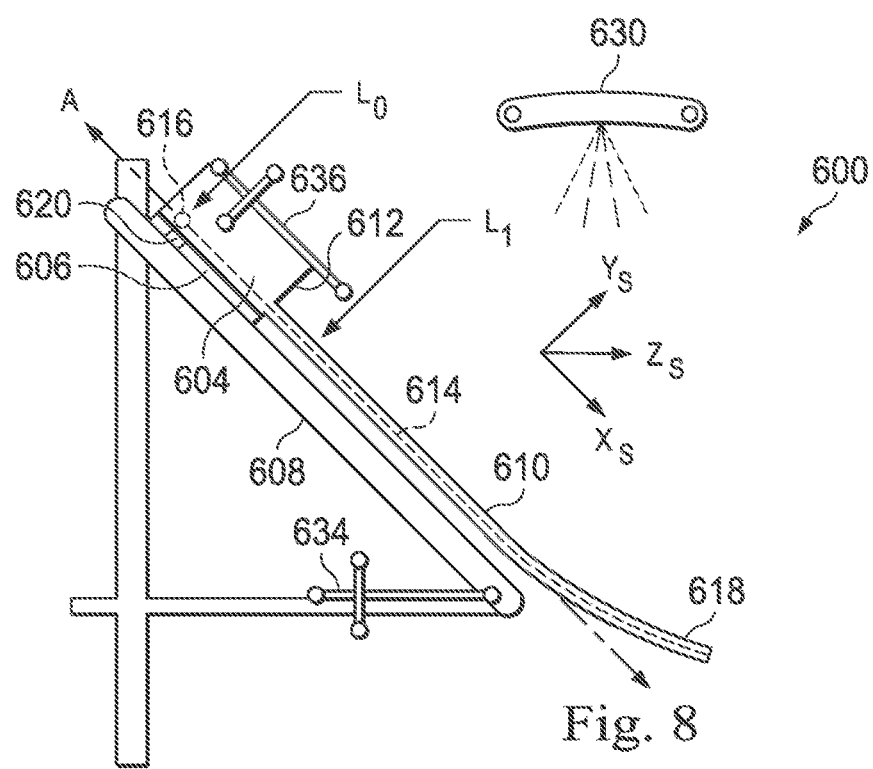
FIG. 8 is a side view of a patient coordinate space including a medical instrument mounted on an insertion track and an optical tracking system used in a calibration procedure according to an embodiment of the present disclosure.

FIG. 8 illustrates the arrangement of the surgical environment during the calibration phase, in accordance with an embodiment of the present disclosure. At a process 712, the optical tracking sensor 630 tracks the set of optical fiducial markers 636 attached to the rigid instrument body 612 as the instrument body moves along the insertion stage 608. At a process 714, the optical tracking sensor 630 tracks the set of optical fiducial markers 634 which are located on the insertion stage 608 of the teleoperational manipulator assembly. In this embodiment, the markers 634 are located at a distal end of the insertion stage 608 near the patient orifice where the catheter 610 enters the patient anatomy.

At a process 716, a calibration procedure is performed to calibrate a relative position and/or orientation of the sensor reference point 616 along an insertion path. Process 716 can be performed before an arrival of the patient anatomy to the surgical environment; that is, process 716 can be performed in whole or in part before the actual surgical operation where the patient is present in the operating room. Alternatively, part or all of process 716 can be performed while the patient is present in the operating room. For example, the position and orientation of the point 616 may be determined by optically tracking the fiducial markers 636 as the carriage 606 moves from a retracted insertion position with the point 616 at location $L_0$ to an advanced insertion position with the point 616 at the location $L_1$. The calibration procedure determines the position and orientation of the point 616 in the surgical environment for a plurality of insertion measurements of the position measuring device 620 (e.g., an encoder). In this embodiment, where the insertion stage 608 restricts movement of the carriage 606 to a linear path, the calibration procedure determines the position and orientation of the point 616 along the direction of the linear path. Thus, the position and orientation of the point 616 in the surgical environment 600 may be determined for a subset or every corresponding insertion measurement of the position measuring device 620. This position and orientation information may be stored, for example, in the form of a calibration table. In alternative embodiments, the insertion stage may have a predefined curved or otherwise non-linear shape.

At a process 718, the position and orientation of the patient P within the surgical environment is determined. The position and orientation of the patient P in the surgical environment may be determined by optical measurement of the set of fiducial markers 632 or by other measurement tools. Thus, any appropriate measurement method can be used to determine the position and orientation information. For example, motor positions may be correlated with when the reference portion of the rigid proximal body is at respective positions along the insertion track. As additional examples, other measurement tools that can be used include a mechanical tape measure, a laser distance sensor, or electromagnetic sensors.

At a process 720, the medical procedure involving insertion of the flexible catheter into the patient anatomy is initiated. The set of fiducial markers 636 on the rigid instrument body 612 may be disabled (e.g., the sensor 630 turned off, the set of fiducial markers 636 removed or obscured, tracking data for the set of fiducial markers 636 gathered but ignored, the set of fiducial markers 636 not tracked by the sensor 630 even though the sensor 630 is operating, or the like) during the medical procedure. As shown in FIG. 9, if the patient P is mobile, the set of fiducial markers 632 may continue to be tracked by the optical tracking sensor 620. Similarly, if the teleoperational manipulator assembly is mobile, the set of fiducial markers 634 may continue to be tracked by the optical tracking sensor 620. As shown in FIG. 10, if the patient P and the teleoperational manipulator assembly are stationary in the surgical environment, the set of fiducial markers 632 may also be disabled (not powered, not operated to track, or tracking information not used), and the pose may be determined without accounting for any changes in patient anatomy relative to the insertion track or the medical instrument guided by the insertion track. Thus, when the patient P is stationary, the optical tracking system may be disabled, eliminating the need to maintain clear lines of sight between some or all fiducial markers of the sets of fiducial markers 632, 634, 636 and the tracking sensor 620. At process 720, the teleoperational assembly moves the rigid instrument body 612 such that the reference point 616 is located at location $L_1$ on the axis A. At the location $L_1$, a measurement from the position measuring device 620 is determined.

At a process 721, shape information from the shape sensor 614 is received when the reference point 616 is at the location $L_1$. The shape information describes the shape of the shape sensor 614 extending between the reference point 616 on the rigid instrument body and the distal end of the flexible catheter 610. At a process 722, the insertion measurement from the position measuring device 620 when the reference portion 616 is at the location $L_1$, is used to reference the calibration information (e.g., the calibration table) established at process 716 to determine the position and orientation of the reference portion 616 in the surgical environment 600. The shape information combined with the location of the reference point 616 in the surgical environment can be used to determine the position and orientation of the distal tip of the flexible catheter 610 and other points along the catheter 610 in the surgical environment.

At a process 724, the flexible catheter 610 is localized with respect to the patient anatomy in the surgical environment. With the patient either tracked or stationary, the position and orientation of the patient P can be determined in the surgical environment. The position and orientation of the flexible catheter 610 can be determined with respect to surgical environment frame of reference from process 722. With both the pose of the distal end of the catheter and the pose of the patient in the surgical environment having been determined, the instrument distal end may be localized with respect to the patient anatomy. The processes 720-724 may be repeated regularly, irregularly, or as manually controlled throughout the medical procedure to localize the flexible catheter when the reference point 616 is at any location along the axis A that has been calibrated.

Figure 11:
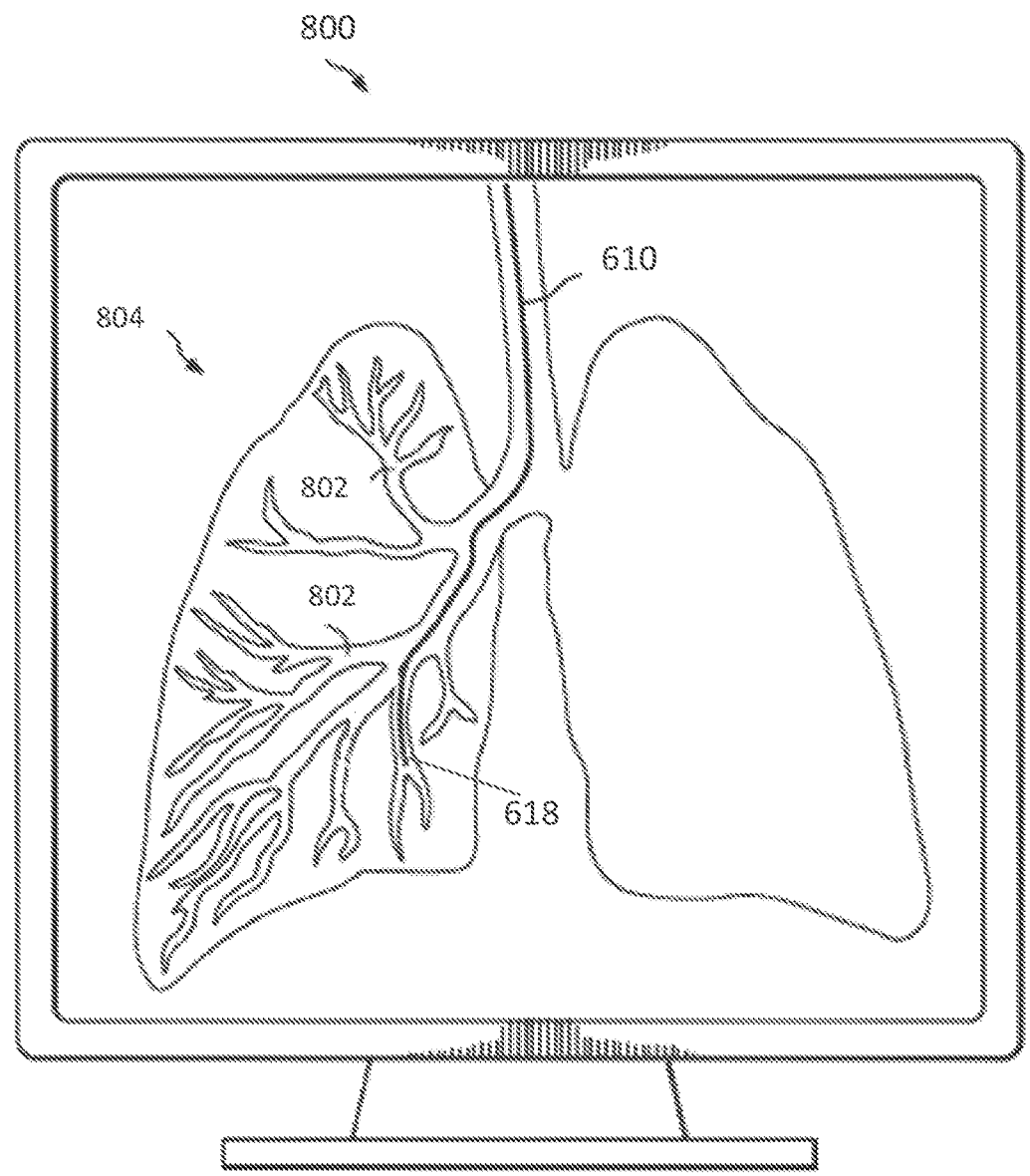
FIG. 11 illustrates a display stage of a registration technique according to an embodiment of the present disclosure.

After localizing the medical instrument to the patient anatomy as described in methods 700 and 710, the medical procedure may be performed with image guidance from the anatomic model as described above at process 458 of FIG. 4. FIG. 11 illustrates a display system 800 in accordance with an embodiment of the present disclosure that displays an image of the medical instrument 610 localized relative to the anatomic model 804 of the patient anatomy. More specifically, the display system 800 displays a rendering of anatomic passageways 802 of a modeled patient lung 804. Model information about the anatomic model 804 of the patient anatomy may be received or measured by a control system. In some embodiments, the control system (e.g. the control system 112) is configured to generate a combined image of catheter registered with an image of the patient anatomy using the model information. With the model reference frame registered to the surgical reference frame according to known model registration techniques, the current shape of the catheter 610 and the location of the distal end 618 may be located in the surgical reference frame and displayed concurrently with the rendering of the passageways 802. Methods for registering the anatomic model information to the patient and/or surgical reference frame are described, for example, in U.S. Provisional Pat. App. No. 62/165,249 filed May 22, 2015; U.S. Provisional Pat. App. No. 62/205,440 filed Aug. 14, 2015; and U.S. Provisional Pat. App. No. 62/205,433 filed Aug. 15, 2015, all of which are incorporated herein by reference in their entirety. Additionally or alternatively, a display of the modeled anatomy from the perspective of the position and orientation of the distal end 618 of the instrument may be displayed to provide the clinician with a pseudo-endoscopic view of the patient anatomy from the perspective of the instrument distal end.

Figure 12:
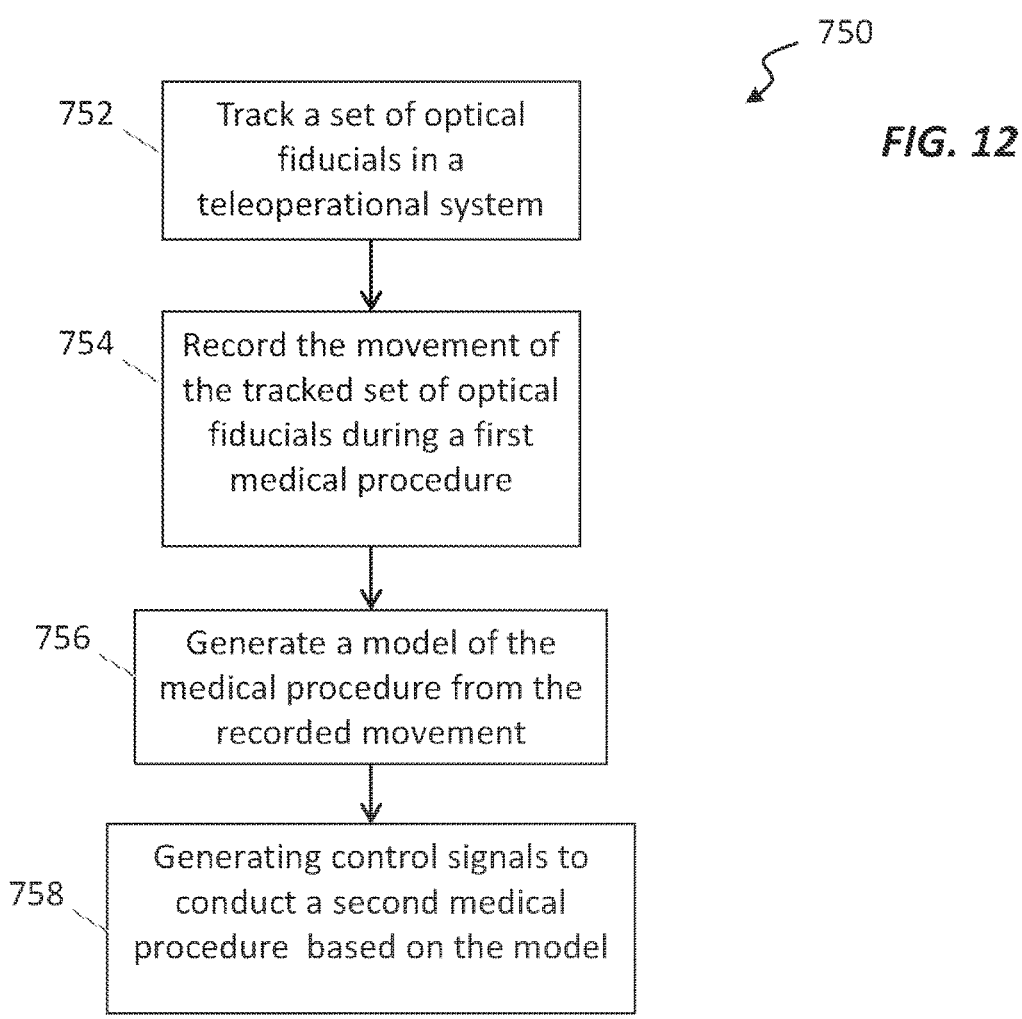
FIG. 12 illustrates a flowchart of a modeled motion portion of a medical procedure according to an embodiment of the present disclosure.

FIG. 12 illustrates a method 750 in accordance with an embodiment of the preset disclosure, of using the optical tracking system of FIG. 6 to create a motion model for the medical instrument. The model may be used to repeat the modeled motion one or more times during a medical procedure. At a process 752, the optical sensor 630 tracks the motion of the set of fiducial markers 636 and/or 634 during a procedure in which the medical instrument 604 is moved through a series of locations along the axis A. The procedure may be performed on the patient P or may be performed without a patient present. At a process 754, the movements observed by the tracking sensor 630 are recorded and stored in a memory. At a process 756 a motion model is generated from the recorded movements. The model may be a set of instructions that may be stored in non-transitory processor readable storage medium, and be capable of being executed by a processor, like a processor of the control system 112, to replicate the recorded motion. At a process 758, controls signals are generated to cause the teleoperational system to repeat the modeled motion.

One or more elements in embodiments of the invention may be implemented in software to execute on a processor of a computer system such as control system 112. When implemented in software, the elements of the embodiments of the invention comprise the code segments to perform the necessary tasks. The program or code segments can be stored in a non-transitory processor readable storage medium or device, including any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system, comprising:
   a medical instrument including:
      an elongated flexible body with a distal end; and
      a rigid proximal body comprising a reference portion;
   a teleoperational manipulator including a position measuring device, the teleoperational manipulator configured to move the rigid proximal body along a defined linear path; and
   a control system configured to:
   track a first set of optical fiducials positioned on the reference portion to produce first optical fiducial information;
   track a second set of optical fiducials fixedly positioned on a portion of the teleoperational manipulator defining the defined linear path to produce second optical fiducial information;
   calibrate a plurality of insertion measurements with respective positions of the reference portion of the rigid proximal body along the defined linear path with the position measuring device; and
   determine a pose of the elongated flexible body with respect to a patient anatomy when the rigid proximal body is at a first location along the defined linear path based on the first location, the plurality of calibrated insertion measurements, and a pose of the patient anatomy.

2. The medical system of claim 1, wherein the control system is further configured to determine the pose of the patient anatomy by tracking a third set of optical fiducials positioned on the patient anatomy.

3. The medical system of claim 2, wherein the control system is further configured to disable the tracking of at least one of the first, the second, or the third sets of optical fiducials.

4. The medical system of claim 1, wherein the control system is further configured to:
   drive movement of the rigid proximal body along the defined linear path; and
   while driving movement of the rigid proximal body along the defined linear path, track the second set of optical fiducials and a third set of optical fiducials positioned on the patient anatomy.

5. The medical system of claim 4, wherein the control system is further configured to determine the pose of the elongated flexible body with respect to the patient anatomy by:
   receiving a calibrated first insertion measurement of the plurality of calibrated insertion measurements when the rigid proximal body of the medical instrument is at the first location;
   receiving shape information from a shape sensor extending within the medical instrument when the rigid proximal body is at the first location;
   receiving tracking information for the third set of optical fiducials when the rigid proximal body of the medical instrument is at the first location; and
   receiving second optical fiducial information for the second set of optical fiducials when the rigid proximal body of the medical instrument is at the first location.

6. The medical system of claim 1, wherein the control system is further configured to receive shape information from a shape sensor extending along at least a portion of the medical instrument, wherein the shape sensor comprises an optical fiber shape sensor or a plurality of electromagnetic sensors.

7. The medical system of claim 6, wherein the control system is further configured to determine a pose of the distal end of the elongated flexible body with respect to the patient anatomy based on the shape information and a pose of the reference portion at the first location.

8. The medical system of claim 1, wherein the control system is further configured to:
   generate a combined image of the elongated flexible body registered with an image of the patient anatomy; and
   cause display of the combined image.

9. The medical system of claim 1, wherein the control system is configured to track the first and second sets of optical fiducials by monitoring the first and second sets of optical fiducials with an optical tracking camera system.

10. The medical system of claim 1, wherein the control system is configured to calibrate the plurality of insertion measurements prior to an arrival of the patient anatomy to a surgical environment in which the medical system is disposed.

11. A non-transitory computer-readable medium storing instructions that, when executed by one or more processors of a control system, cause the one or more processors to:
   track a first set of optical fiducials positioned on a reference portion of a medical instrument to produce first optical fiducial information, the medical instrument including:
      an elongated flexible body with a distal end; and
      a rigid proximal body comprising a reference portion;
   track a second set of optical fiducials fixedly positioned on a portion of a teleoperational manipulator defining a defined linear path along which the rigid proximal body moves to produce second optical fiducial information;
   calibrate a plurality of insertion measurements with respective positions of the reference portion of the rigid proximal body along the defined linear path with a position measuring device of the teleoperational manipulator; and
   determine a pose of the elongated flexible body with respect to a patient anatomy when the rigid proximal body is at a first location along the defined linear path based on the first location, the plurality of calibrated insertion measurements, and a pose of the patient anatomy.

12. The non-transitory computer-readable medium of claim 11, further storing instructions that, when executed by the one or more processors, cause the one or more processors to:

determine the pose of the patient anatomy by tracking a third set of optical fiducials positioned on the patient anatomy.

13. The non-transitory computer-readable medium of claim 12, further storing instructions that, when executed by the one or more processors, cause the one or more processors to:
disable the tracking of at least one of the first, the second, or the third sets of optical fiducials.

14. The non-transitory computer-readable medium of claim 11, further storing instructions that, when executed by the one or more processors, cause the one or more processors to:
drive movement of the rigid proximal body along the defined linear path; and
while driving movement of the rigid proximal body along the defined linear path, track the second set of optical fiducials and a third set of optical fiducials positioned on the patient anatomy.

15. The non-transitory computer-readable medium of claim 14, further storing instructions that, when executed by the one or more processors, cause the one or more processors to:
determine the pose of the elongated flexible body with respect to the patient anatomy by:
receiving a calibrated first insertion measurement of the plurality of calibrated insertion measurements when the rigid proximal body of the medical instrument is at the first location;
receiving shape information from a shape sensor extending within the medical instrument when the rigid proximal body is at the first location;
receiving tracking information for the third set of optical fiducials when the rigid proximal body of the medical instrument is at the first location; and
receiving second optical fiducial information for the second set of optical fiducials when the rigid proximal body of the medical instrument is at the first location.

16. The non-transitory computer-readable medium of claim 11, further storing instructions that, when executed by the one or more processors, cause the one or more processors to:
receive shape information from a shape sensor extending along at least a portion of the medical instrument, wherein the shape sensor comprises an optical fiber shape sensor or a plurality of electromagnetic sensors.

17. The non-transitory computer-readable medium of claim 16, further storing instructions that, when executed by the one or more processors, cause the one or more processors to:
determine a pose of the distal end of the elongated flexible body with respect to the patient anatomy based on the shape information and a pose of the reference portion at the first location.

18. The non-transitory computer-readable medium of claim 11, further storing instructions that, when executed by the one or more processors, cause the one or more processors to:
generate a combined image of the elongated flexible body registered with an image of the patient anatomy; and
cause display of the combined image.

19. The non-transitory computer-readable medium of claim 11, further storing instructions that, when executed by the one or more processors, cause the one or more processors to:
track the first and second sets of optical fiducials by monitoring the first and second sets of optical fiducials with an optical tracking camera system.

20. The non-transitory computer-readable medium of claim 11, further storing instructions that, when executed by the one or more processors, cause the one or more processors to:
calibrate the plurality of insertion measurements prior to an arrival of the patient anatomy to a surgical environment in which the control system is disposed.

\* \* \* \* \*